United States Patent [19]

Hansen et al.

[11] Patent Number: 5,731,177
[45] Date of Patent: Mar. 24, 1998

[54] PROCESS FOR DEMETHYLATING DIMETHYLSULFONIUM COMPOUNDS

[75] Inventors: Theo Adriaan Hansen, Groningen; Marc Jos E. C. van der Maarel, Haren, both of Netherlands

[73] Assignee: Quest International B.V., Naarden, Netherlands

[21] Appl. No.: 549,772

[22] PCT Filed: May 16, 1994

[86] PCT No.: PCT/EP94/01640
§ 371 Date: Nov. 14, 1995
§ 102(e) Date: Nov. 14, 1995

[87] PCT Pub. No.: WO94/26918
PCT Pub. Date: Nov. 24, 1994

[30] Foreign Application Priority Data

May 14, 1993 [EP] European Pat. Off. ............ 93201389

[51] Int. Cl.$^6$ .............. C12P 11/00; C12P 7/40; C12P 7/04; C12P 1/04
[52] U.S. Cl. .............. 435/130; 435/136; 435/157; 435/170
[58] Field of Search .............. 435/130, 136, 435/170, 157

[56] References Cited

PUBLICATIONS van der Maarel et al. 1993 Arch. Microbiol. vol. 160 pp. 411–412.
Heijthujsen et al. 1989. Arch. Microbiol. vol. 152 pp. 393–396.
Kiene et al. 1988. Appl. Environ. Microbiol. vol. 54 pp. 2208–2212.
Visscher et al. 1991. Appl. Envir. Microbiol. vol. 57, pp. 3237–3242.
Visscher et al. 1992. Mar. Ecol. Prog. Ser. vol. 189 (2–3) pp. 293–296.

*Primary Examiner*—Leon B. Lankford, Jr.
*Assistant Examiner*—Christopher R. Tate
*Attorney, Agent, or Firm*—Cushman Darby & Cushman IP Group Pillsbury Madison & Sutro LLP

[57] ABSTRACT

Process for preparing S-methylmercapto and mercapto compounds comprising the step of demethylating a dimethylsulfonium compound of formula I to the corresponding S-methylmercapto compound of formula II, using a microorganism or alga which is capable of demethylating 3-dimethylsulfonium propionate (DMSP) to S-methyl-3-mercaptopropionate (MMPA), but which is incapable of further demethylating the latter compound to 3-mercaptopropionate with the same speed, or using an enzyme preparation derivable from such microorganism or alga:

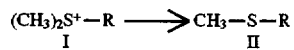

$$(CH_3)_2S^+ - R \longrightarrow CH_3 - S - R$$
$$\quad\quad I \quad\quad\quad\quad\quad\quad II$$

Preferably the group R denotes $CH_2-CH_2-COOH$ (I is DMSP), $CH_2-CH(NH_2)-COOH$ (I is S-dimethylcystein), $CH_2-Ch_2-CH(NH_2)-COOH$ (I is S-methylmethionine) or $CH_2-COOH$ (I is 2-dimethylsulfonium acetate), or a salt or ester of any of these. The microorganisms are preferably marine Desulfobacterium strains, especially a *Desulfobacterium autotrophicum, Desulfobacterium vacuolatum* or similar strain.

5 Claims, No Drawings

PROCESS FOR DEMETHYLATING DIMETHYLSULFONIUM COMPOUNDS

This application claims benefit of international application PCT/EP94/01640, filed May 16, 1994.

The invention concerns a process demethylating dimethyl-sulphonium compounds. More particularly the inventions concerns a process for microbiologically demethylating dimethylsulfonium compounds to the corresponding S-methyl-mercapto compounds, such as 3-dimethylsufonium propionate to S-methyl-3-mercaptopropionate.

Various S-methylmercapto compounds are either useful as flavour components themselves or as intermediates therefor. Thus, S-methyl-3-mercaptopropionate (hereinafter referred to as MMPA for convenience) may be converted into its alkyl esters which are used e.g. in various fruit flavours. Also, MMPA may be further demethylated to 3-mercaptopropionate (hereinafter referred to as MPA for convenience) the esters of which are also used as flavour components.

MMPA is known to be an intermediate in the-degradation of 3-dimethylsulfonium propionate (also known as dimethyl-β-propiothetin, but hereinafter referred to as DMSP for convenience) in anoxic marine coastal sediments. A product of this degradation pathway is MPA and it was shown by R. P. Kiene and B. F. Taylor, Appl. Environ. Microbiol. 54:2208–2212, and Nature 332:148–150, that MMPA is converted to MPA at a rate similar to that of the conversion of DMSP to MMPA. MMPA and MPA are also intermediates in the metabolism of DMSP by certain aerobic bacteria, whereas other aerobic bacteria are known to degrade DMSP via an initial cleavage to acrylate and dimethyl sulfide (B. F. Taylor and D. C. Gilchrist, Appl. Environ. Microbiol. 57:3581–3584). Thus, although in theory DMSP might be the starting material for preparing MMPA, this so far appeared to be impossible due to the immediate further degradation to MPA. Moreover, although The DMSP - MMPA - MPA conversion was known to take place in coastal sediment, the microorganisms responsible for this degradation were unknown.

It is also known, as already indicated above, that DMSP can be cleaved to dimethylsulfide and acrylate and this process is known from many literature sources to take place in various marine organisms, especially algae. The process has been described in JP-A-63/222670 as a useful source of dimethylsulphide for flavouring purposes. This Japanese patent application also describes various useful sources of DMSP, including various marine organisms and especially algae. Finally it describes how DMSP may be isolated from these sources. However, it does not describe the conversion of DMSP in MMPA or MPA. It has now been found, however, that S-methylmercapto compounds and mercapto compounds can be prepared using a process which comprises the step of demethylating a dimethylsulfonium compound of general formula I to the corresponding S-methylmercapto compounds of general formula II, using a microorganism or alga which is capable of demethylating DMSP to MMPA, but which is incapable of further demethylating MMPA to MPA with the-same or comparable speed, or using an enzyme preparation derivable from such microorganism.

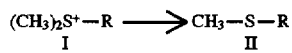

$$(CH_3)_2S^+—R \longrightarrow CH_3—S—R$$
$$\quad I \qquad\qquad\qquad II$$

In these general formulae R denotes an alkyl radical derived from an alkane carboxylic acid or a derivative thereof. Examples of such radicals are: $CH_2—CH_2—COOH$ (I is DMSP), $CH_2—CH(NH_2)—COOH$ (I is S-dimethylcystein), $CH_2—CH_2—CH(NH_2)—COOH$ (I is S-methylmethionine) and $CH_2—COOH$ (I is 2-dimethylsulphonium acetate, also known as dimethylthetin) and salts or esters of any of these. Such starting materials and various others for the demethylation according to the invention can be found in nature e.g. in various marine organisms and in brassica species and asparagus.

In the process the S-methylmercapto reaction product accumulates in the medium in which the microorganism is cultivated, respectively in the reaction medium in which the enzymatic reaction is carried out, and which contains the dimethylsulfonium compound. The reaction product can be isolated therefrom. The process is especially useful for converting DMSP into MMPA or derivatives of DMSP into the corresponding derivative of MMPA.

Particularly suitable microorganisms are anaerobic and belong to the group of sulfate reducing microorganisms such as can be found in marine (especially coastal), estuarine and freshwater sediments. Desulfobacterium strains are especially useful, such as *Desulfobacterium autotrophicum*, *Desulfobacterium vacuolatum* and similar microorganisms. Examples of such microorganisms are Desulfobacterium PM4 (DSM 8278), *Desulfobacterium vacuolatum* (DSM 3385) and *Desulfobacterium autotrophicum* WN. The isolation and characterization of Desulfobacterium PM4, were recently described by J.H.F.G. Heijthuijsen and T. A. Hansen, Arch. Microbiol.(1989) 152:393–396, however, without mentioning their ability to metabolize DMSP. Desulfobacterium PM4 is rather similar to *Desulfobacterium autotrophicum* and *Desulfobacterium vacuolatum*. Other suitable microorganisms may be found among the acetogenic bacteria, especially those which are known to metabolize betaine to dimethylglycine.

The microorganisms or algae are grown under conditions adapted to the type of microorganism or alga involved. Thus, the anaerobic sulfate reducing microorganisms are grown under anaerobic conditions in the presence of suitable carbon, nitrogen and other nutrient sources, such as yeast extract, and a suitable sulfate source such as $Na_2SO_4$. Certain suitable microorganisms may be able to grow using the dimethylsulfonium compound as the only or main carbon or energy source.

The dimethylsulfonium compound (the substrate), e.g. DMSP, is present in the culture medium from the start and/or added to the medium during culturing while care is taken that the substrate concentration does not exceed the level which may retard the growth of the microorganism or alga. Sulfides may be produced in a side reaction (depending on the microorganism used) and should be removed in a suitable way if their accumulation would retard the growth of the microorganism.

As indicated above, the demethylation of the substrate may also be carried out using an enzyme preparation derivable from microorganisms or algae capable of performing this reaction. Such enzyme preparation may be obtained directly from these microorganisms, e.g. in the form of homogenized or lysed cells or a further purified product prepared thereof. Also, suitable enzyme preparations may be obtained from other microorganisms after they have been subjected to a genetic engineering process which enables them to make the enzymes necessary for the demethylation. In carrying out such genetic engineering process the information on the structure of the pertinent enzymes present in the original microorganisms or algae capable of performing the reaction is used.

The reaction product of the demethylation reaction according to the invention, including the S-methylmercapto compound, e.g. MMPA, may be removed from the culture or reaction medium in any suitable way, such as by extraction with a suitable organic solvent, by distillation, by filtration or centrifugation, or by a suitable chromatographic means. If accumulation of the S-methylmercapto compound retards the growth of the microorganism or alga, this removal should be done simultaneously with the culturing.

If necessary or desirable the S-methylmercapto compound may be further separated or purified from other components possibly present in the reaction product. This purification may be done by methods known in the art.

The S-methylmercapto compound may be used as a flavour component as such or after further conversion, e.g. depending on the nature of the group R. Thus, MMPA may be converted into the corresponding esters, especially the lower alkyl esters in various ways known in the art. Alternatively it may be further degraded into MPA in ways known in the art e.g. using a microorganism which is known to degrade DMSP and/or MMPA to MPA. The MPA thus obtained may be converted into its esters, especially the lower alkyl esters, in ways known in the art.

The MMPA or MPA esters, or other compounds obtained by the demethylation reaction according to the invention, may be used as flavour components in various flavourings and foodstuffs. To this end they may be combined with other flavour components, and if desired with auxiliary substances, solvents, powdered carriers or substrates, in ways known in the art.

In certain cases other sulfur compounds, e.g. dimethylsulfide, may be formed in side reactions during the demethylation process according to the invention and thus be present in the reaction product. From a point of view of use of the reaction product for flavouring purposes, such compounds may sometimes be left in the reaction product because they also may give a useful flavour contribution.

Thus, the product of the process according to the invention may be a reaction product rich in S-methylmercapto compound and possibly other components derived from side reactions, or a further purified S-methylmercapto compound, depending on the type of separation step and/or degree of purification used in the process. Alternatively, the process may comprise further steps such as chemically or microbiologically/enzymatically converting the S-methylmercapto compound into derivatives thereof or into the corresponding mercapto compound or derivatives thereof.

Flavour components which may be advantageously combined in flavourings and foodstuffs with the S-methylmercapto compounds according to the invention are: natural products such as extracts, essential oils, absolutes, resins, concretes, fruit juices, etc., but also synthetic components such as hydrocarbons, alcohols, aldehydes, ketones, esters, ethers, acetals, ketals, acids, etc., including saturated and unsaturated compounds, aliphatic, alicyclic and heterocyclic compounds. Such flavour components are mentioned, for example, in S. Arctander, Perfume and Flavor Chemicals (Montclair, N.J., 1969), in S. Arctander, Perfume and Flavor Materials of Natural Origin (Elizabeth, N.J., 1960), in T. E. Furia et al., CRC Fenaroli's Handbook of Flavor Ingredients, 2nd edition (Cleveland, CRC Press Inc., 1975), H. B. Heath, Source Book of Flavours, The Avi Publishing Co. Inc. Westport, Conn. (1981) and in "Flavor and Fragrance Materials - 1989", Allured Publishing Co. Wheaton, Ill. USA. Auxiliary substances and solvents which can be used in flavour compositions containing the S-methylmercapto compounds according to the invention are, for example: ethanol, isopropanol, diethyleneglycol monoethyl ether, glycerol, triacetin etc. Powdered substrates or carriers may include salt, starch derivatives and the like. Processing into a powdered product may include spray-drying and other techniques of micro-encapsulation.

EXAMPLE 1

Desulfobacterium PM4 (deposited under The Budapest Treaty with the Deutsche Sammlung von Mikroorganismen und Zellkulturen in Braunschweig, No. DSM 8278) was isolated and cultured as described in Arch. Microbiol (1989) 152: 393–396. A mineral medium (Ph 7.2) with yeast extract (0.02% w/w) and 20 mM $Na_2SO_4$ in a completely filled culture vessel was used which was inoculated with 1 ml of a preculture containing approximately $10^8$ cells, and to which 2.7 g/l (20 Mm) DMSP was added as a filter-sterilized solution in 1M $NaHCO_3$. Culturing was continued for 1 week at about 20° C., after which the conversion of DMSP was complete. The cells were removed by centrifugation and the MMPA isolated from the culture medium by extraction with diethyl ether. After removal of the solvent 2.3 g (19 Mm) of MMPA was obtained.

EXAMPLE 2

A pineapple flavour was prepared according to the following recipe:

|  | parts by weight |
|---|---|
| Rose oxide | 0.1 |
| Acetic acid | 0.3 |
| Isobutanol | 0.3 |
| Ethyl lactate | 0.3 |
| 2-Methylbutyric acid | 0.3 |
| 2-Methylbutyl acetate | 0.6 |
| Ethyl heptanoate | 0.6 |
| Ethyl butyrate | 0.9 |
| 3-Methylbutyl acetate | 1.2 |
| Methyl 2-methylbutyrate | 1.2 |
| γ-Decalactone | 2.4 |
| Maltol | 3.2 |
| Allyl heptanoate | 3.6 |
| 2,5-Dimethylfuranolon | 4.0 |
| Methyl S-methyl-3-mercaptopropionate | 0.6 |
| Ethanol | 481.0 |
| Water | 499.4 |
| TOTAL | 1000 |

We claim:

1. A process for preparing methyl mercaptopropionate which comprises demethylating dimethylsulfonium propionate using a bacterial strain of the Desulfobacterium genus, said strain being essentially incapable of further demethylating the methyl mercaptopropionate to mercaptopropionate.

2. A process according to claim 1 wherein the bacterial strain is a marine Desulfobacterium strain.

3. A process according to claim 1 wherein the Desulfobacterium strain is *Desulfobacterium autotrophicum* or *Desulfobacterium vacuolatum*.

4. A process according to claim 2 wherein the Desulfobacterium strain is Desulfobacterium PM4 (DSM 8278), *Desulfobacterium autotrophicum* WN, or *Desulfobacterium vacuolatum* (DSM 3385).

5. A process according to claim 1 wherein the strain is Desulfobacterium PM4.

* * * * *